United States Patent
Yaginuma

(10) Patent No.: US 9,804,186 B2
(45) Date of Patent: Oct. 31, 2017

(54) LIQUID SUCTION TOOL, LIQUID SUPPLY UNIT AND AUTOMATED ANALYZER

(71) Applicant: JEOL Ltd., Tokyo (JP)

(72) Inventor: Takashi Yaginuma, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/938,150

(22) Filed: Nov. 11, 2015

(65) Prior Publication Data

US 2016/0187364 A1 Jun. 30, 2016

(30) Foreign Application Priority Data

Nov. 11, 2014 (JP) ................................ 2014-228704

(51) Int. Cl.
*G01N 35/10* (2006.01)
*B01L 3/00* (2006.01)

(52) U.S. Cl.
CPC .......... *G01N 35/1016* (2013.01); *B01L 3/523* (2013.01); *B01L 2200/026* (2013.01); *B01L 2300/123* (2013.01); *B01L 2400/049* (2013.01); *G01N 35/1002* (2013.01); *G01N 2035/1027* (2013.01)

(58) Field of Classification Search
CPC ........ B01L 3/02; B01L 3/0241; B01L 3/0244; B01L 2300/0838; B01L 2300/0832; G01N 35/1016; G01N 35/1002; G01N 2035/1027
USPC .................................. 600/408; 422/500–570
See application file for complete search history.

(56) References Cited

U.S. PATENT DOCUMENTS

| | | | | |
|---|---|---|---|---|
| 4,637,934 A * | 1/1987 | White | ..................... | A61J 9/005 215/11.1 |
| 5,307,696 A * | 5/1994 | Allain | ..................... | G01N 1/10 141/131 |
| 5,526,853 A * | 6/1996 | McPhee | ................. | A61J 1/2089 141/114 |
| 5,551,312 A * | 9/1996 | Masson | ................ | B01J 19/0053 73/863.81 |
| 5,570,815 A * | 11/1996 | Ramsay | ............... | B67D 7/0255 222/105 |
| 5,885,532 A * | 3/1999 | Maltabes | ............ | A61M 5/1412 422/106 |
| 6,726,672 B1 * | 4/2004 | Hanly | ....................... | A61J 1/10 215/247 |
| 8,043,582 B2 * | 10/2011 | Bauer | ................... | B01L 3/0262 422/500 |
| 8,052,618 B2 * | 11/2011 | Haar | ................... | A61B 5/14532 600/583 |
| 8,282,881 B2 * | 10/2012 | Takahashi | ................ | G01N 1/31 422/400 |

(Continued)

FOREIGN PATENT DOCUMENTS

JP 2005181309 A 7/2005
JP 2011179954 A 9/2011

*Primary Examiner* — Brian R Gordon
(74) *Attorney, Agent, or Firm* — The Webb Law Firm

(57) ABSTRACT

The liquid suction tool, liquid supply unit and automated analyzer can reduce an amount of the liquid remaining in the suction conduit while maintaining the strength of the suction conduit. The liquid suction tool 12 has a rod-like suction conduit 31 and a connecting member 32. The suction conduit 31 is inserted into the storage bag 21. A groove 34 is formed on a side surface of the suction conduit 31 to pass the liquid.

5 Claims, 9 Drawing Sheets

(56) References Cited

U.S. PATENT DOCUMENTS

| | | | | |
|---|---|---|---|---|
| 8,338,187 B2* | 12/2012 | DeRosier | G01N 35/028 | 422/407 |
| 8,539,905 B2* | 9/2013 | Cady | B01L 3/0248 | 118/300 |
| 8,778,279 B2* | 7/2014 | Durack | B01L 3/5027 | 422/407 |
| 8,876,790 B2* | 11/2014 | Rahimy | A61J 1/20 | 604/403 |
| 8,961,901 B2* | 2/2015 | Glauser | A61B 5/1411 | 422/500 |
| 2002/0094304 A1* | 7/2002 | Yang | B01J 19/0046 | 422/400 |
| 2002/0115981 A1* | 8/2002 | Wessman | A61M 5/1411 | 604/411 |
| 2003/0148539 A1* | 8/2003 | van Dam | B01L 3/0244 | 436/180 |
| 2003/0215368 A1* | 11/2003 | Ito | B01L 3/0244 | 422/507 |
| 2005/0209737 A1* | 9/2005 | Kircher | B01F 13/1063 | 700/266 |
| 2005/0236566 A1* | 10/2005 | Liu | B82B 3/00 | 250/306 |
| 2005/0266149 A1* | 12/2005 | Henderson | B01L 3/0244 | 427/2.11 |
| 2011/0034899 A1* | 2/2011 | Thome, Jr. | A61J 1/16 | 604/407 |
| 2015/0290079 A1* | 10/2015 | Nishioka | A61J 1/1406 | 604/408 |
| 2016/0194592 A1* | 7/2016 | Higeta | C12M 29/04 | 422/513 |

\* cited by examiner

LIQUID SUCTION TOOL, LIQUID SUPPLY UNIT AND AUTOMATED ANALYZER

BACKGROUND OF THE INVENTION

Field of the Invention

The present invention relates to a liquid suction tool for sucking a liquid such as a cleaning liquid or reagent, a liquid supply unit having the liquid suction tool, and an automated analyzer having the liquid supply unit.

Description of the Related Art

Conventionally, there has been known an automated analyzer that quantitatively measures the specific substance in a specimen of a biological sample such as blood or urea. The automated analyzer has a liquid storage container which stores a liquid such as a cleaning liquid or a reagent to be used in a measuring device where the measurement of the specimen is carried out. In addition, the liquid is supplied to the measuring device from the liquid storage container via a liquid suction tool.

An example of such a conventional liquid storage container is, for example, one described in Patent Literature 1. Patent Literature 1 discloses a technique provided with a container body having flexibility and a pipe-like tube which is inserted to the container body. In the technique disclosed in Patent Literature 1, a liquid stored in the container body corresponding to a storage bag is sucked by the tube corresponding to the liquid suction tool, and the sucked liquid is supplied to a blood analyzer corresponding to the automated analyzer.

Furthermore, in order to reduce a liquid remaining in the storage bag, Patent Literature 2 discloses a technique that a dispense port that discharges the liquid in the storage bag is directed downward in the vertical direction.

RELATED ART DOCUMENT

Patent Document

Patent Literature 1: Japanese Patent Laid-Open Publication No. 2005-181309
Patent Literature 2: Japanese Patent Laid-Open Publication No. 2011-179954

DISCLOSURE OF THE INVENTION

Problems to be Solved by the Invention

However, according to the technique described in Patent Literature 1, when the container body is deflated by discharging the liquid, the liquid still remains in the cylinder hole of the tube since the opening of the tube is clogged by the inner wall of the container body.

In order reduce an amount of the liquid remaining inside the suction conduit, it is considered that the diameter of the suction conduit is made small and the inner diameter of the cylinder hole through which the liquid passes is also made small. However, when the diameter of the suction conduit is made small, the suction conduit is likely to be bended or broken since the strength of the suction conduit itself is lowered, and thus a problem of suction failure is generated.

In addition, it is also considered that only the inner diameter of the cylinder hole of the suction conduit is made small, but in this case, the cylinder hole is likely to be clogged in producing the suction conduit. Therefore, it was difficult to make only the inner diameter of the cylinder hole of the suction conduit small from the viewpoint of producing the suction conduit.

Furthermore, according to the technique described in Patent Literature 2, a liquid is likely to leak out from a connection portion of the storage bag and the suction conduit, and the leaked-out liquid is further likely to cause failure of a device.

In consideration of the above problems, an object of the present invention is to provide a liquid suction tool that can reduce the liquid remaining in the suction conduit while maintaining the strength of the suction conduit, a liquid supply unit, and an automated analyzer.

SUMMARY OF THE INVENTION

Means for Solving the Problem

In order to solve the above problems to achieve the object of the present invention, the liquid suction tool of the present invention is a liquid suction tool which is attached to a liquid storage container that a liquid to be supplied to a measuring device of an automated analyzer is stored. The liquid suction tool has a suction conduit made in the form of a rod, and a connecting member. The suction conduit is inserted to a storage bag which configures the liquid storage container. The connecting member is fixed at one end portion in the axial direction of the suction conduit, and connects the suction conduit and the storage bag. Further, a groove in which the liquid passes through is formed on a side surface of the suction conduit.

The liquid supply unit of the present invention has a liquid storage container which stores a liquid to be supplied to a measuring device of an automated analyzer, and a liquid suction tool which is attached to the liquid storage container. The liquid storage container has a storage bag to receive the liquid which is made of a sheet member having flexibility and in the form of a bag, and an cylindrical insert provided with the storage bag. The liquid suction tool has a suction conduit which is made in the form of a rod and a connecting member. The suction conduit is inserted into the storage bag through the cylindrical insert. The connecting member is fixed at one end portion in the axial direction of the suction conduit and attached to the cylindrical insert, and connects the suction conduit and the storage bag. Further, a groove in which the liquid passes through is formed on a side surface of the suction conduit.

Furthermore, the automated analyzer of the present invention has a measuring device to measure characteristics of a reaction solution which is obtained by reacting a specimen to be measured and a reagent, and a liquid supply unit to supply a liquid to the measuring device. The liquid supply unit has a liquid storage container to receive the liquid, and a liquid suction tool which is attached to the liquid storage container. The liquid storage container has a storage bag to receive the liquid which is made of a sheet member having flexibility and in the form of a bag, and an cylindrical insert provided with the storage bag. The liquid suction tool has a suction conduit which is made in the form of a rod and a connecting member. The suction conduit is inserted into the storage bag through the cylindrical insert. The connecting member is fixed at one end portion in the axial direction of the suction conduit and attached to the cylindrical insert, and connects the suction conduit and the storage bag. Further, a groove in which the liquid passes through is formed on a side surface of the suction conduit.

Effects of the Invention

According to the liquid suction tool, the liquid supply unit and the automated analyzer of the present invention, it is possible to reduce an amount of the liquid which remains in the suction conduit while maintaining the strength of the suction conduit.

DESCRIPTION OF THE PREFERRED EMBODIMENTS

Hereinafter, the liquid suction tool, the liquid supply unit and the automated analyzer of the present invention will be explained by referring to FIG. 1 to FIG. 11. Note that, in each drawing, the same symbol is attached to the common member. In addition, the explanation is made in the following order, but the present invention is not limited to the following embodiments.
1. First exemplary embodiment
  1-1. Configuration of automated analyzer
  1-2. Configuration of liquid supply unit
  1-3. Operation of liquid supply unit
2. Second exemplary embodiment 1. First Exemplary Embodiment 1-1. Configuration of Automated Analyzer First, the automated analyzer according to the first exemplary embodiment of the present invention (hereinafter, referred to as "exemplary embodiment") will be explained by referring to FIG. 1.

Figure 1:
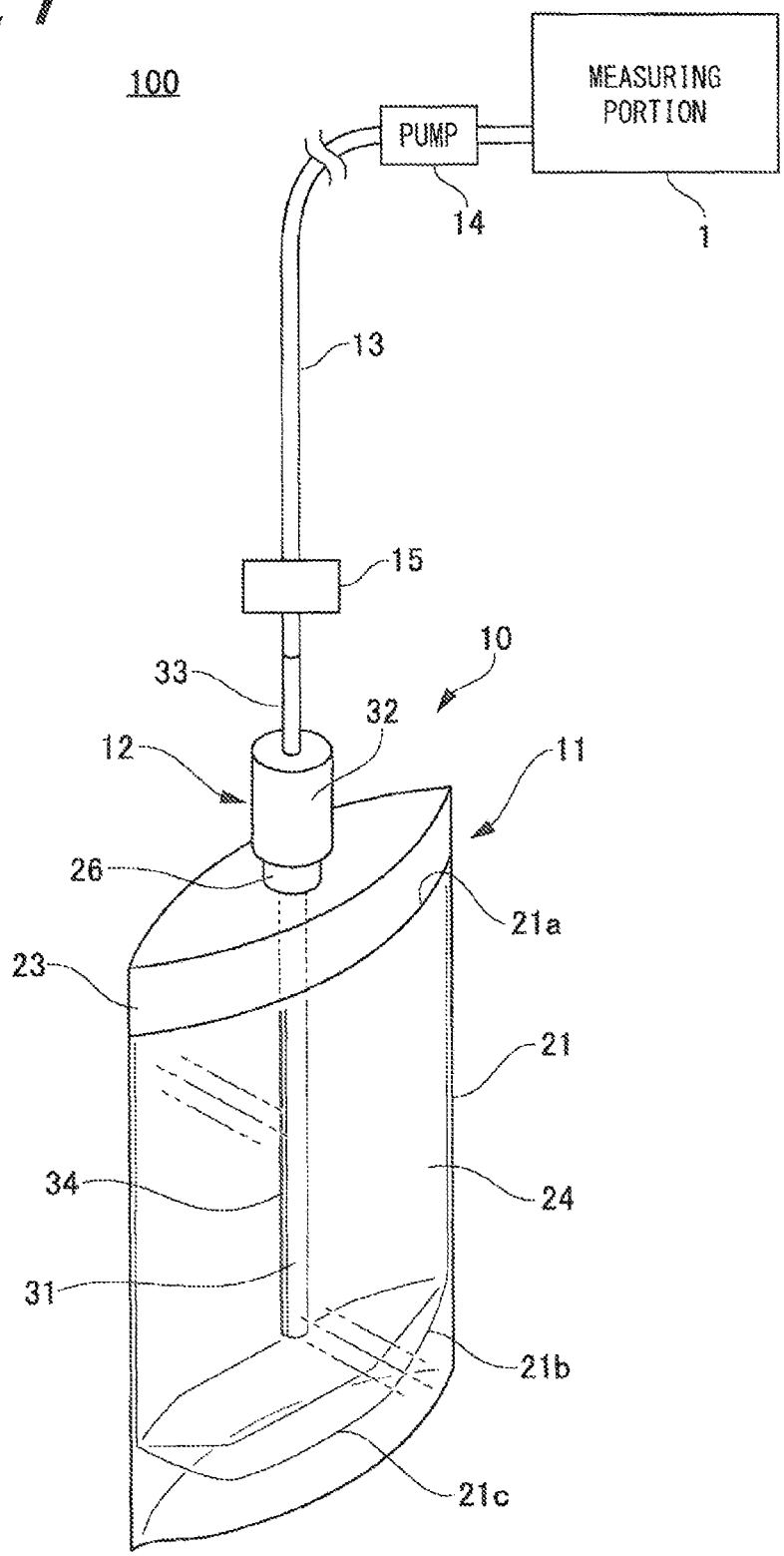
FIG. 1 is a schematic view of the schematic configuration of the automated analyzer according to the first exemplary embodiment of the present invention.

FIG. 1 is an explanatory view which schematically shows the automated analyzer of the exemplary embodiment.

A device shown in FIG. 1 is a biochemical analyzer 100 which is one example of the automated analyzer of the present invention. The biochemical analyzer 100 is a device that automatically measures an amount of the specific component contained in a living sample such as blood or urea. The biochemical analyzer 100 has a measuring device 1 that automatically measures an amount of the specific component contained in a living sample, and a liquid supply unit 10 that stores a liquid supplied to the measuring device 1.

The measuring device 1 measures the characteristics of the reaction solution obtained by stirring a specimen and a reagent and causing the specimen to react with the reagent. The measuring device 1 has a specimen unit that stores the specimen which is a specimen to be measured, a reagent unit that stores the reagent, a dispensing pipette that dispenses the specimen and the reagent, a stirring unit that stirs the reaction solution, and the like. Furthermore, a cleaning liquid for cleaning the dispensing pipette, a stirring bar of the stirring unit, and the reagent unit, and the like; and a liquid such as the reagent stored in the reagent unit are supplied to the measuring device 1 from the liquid supply unit 10.

1-2. Configuration of Liquid Supply Unit

Next, the detailed configuration of the liquid supply unit 10 will be explained by referring to FIG. 1 to FIG. 7.

Figure 2:
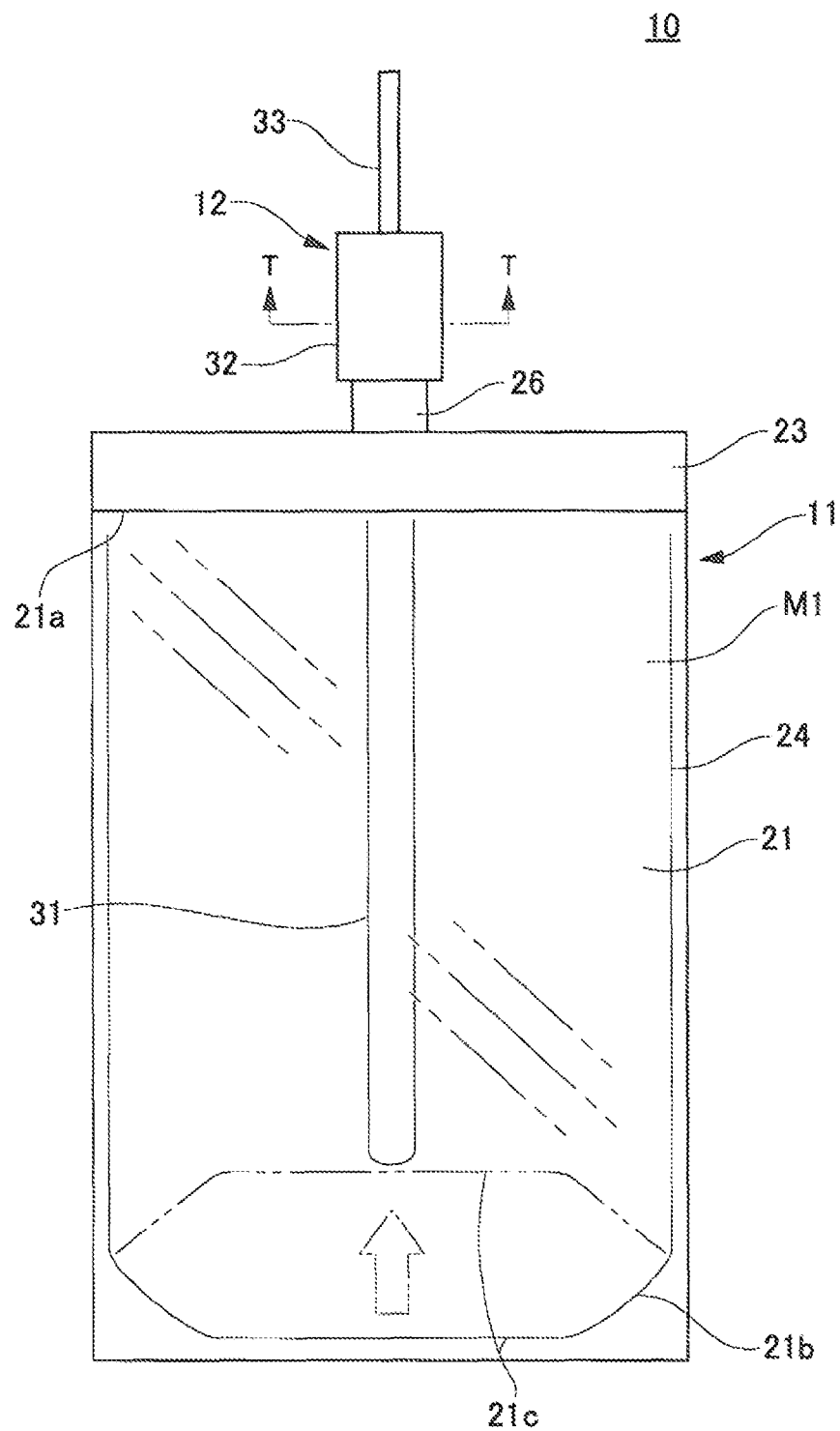
FIG. 2 is a front view of the liquid supply unit according to the first exemplary embodiment of the present invention.
Figure 3:
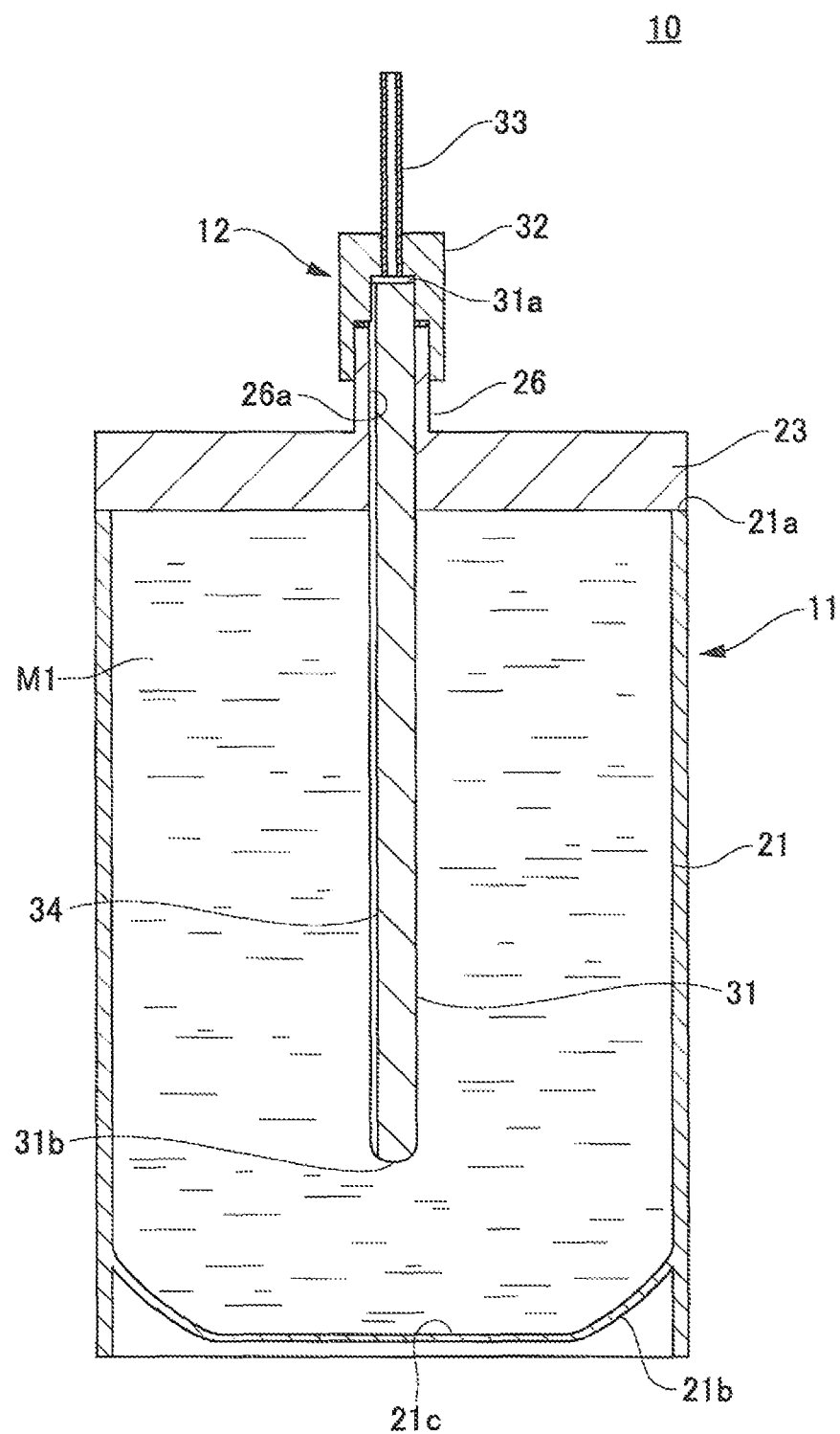
FIG. 3 is a cross-sectional view of the liquid supply unit according to the first exemplary embodiment of the present invention.

FIG. 2 is a front view of the liquid supply unit 10, and FIG. 3 is a cross-sectional view of the liquid supply unit 10.

As shown in FIG. 1 and FIG. 2, the liquid supply unit 10 includes the liquid storage container 11 that stores the liquid and the liquid suction tool 12 attached to the liquid storage container 11. In addition, as shown in FIG. 1, the liquid supply unit 10 is connected to the measuring device 1 via the connecting tube 13. A connecting tube 13 is provided with a suction pump 14 and a pressure sensor 15. The suction pump 14 sucks the liquid stored in the liquid storage container 11 via the connecting tube 13 and the liquid suction tool 12. The pressure sensor 15 detects the pressure of the connecting tube 13.

[Liquid Storage Container]

As shown in FIG. 2, the liquid storage container 11 has the storage bag 21 in which a liquid M1 is filled and a connecting member 23 on a container side which connects to the liquid suction tool 12.

The storage bag 21 is constituted by the sheet member 24 having flexibility. The storage bag 21 is formed in a bag shape by using the sheet member 24. An opening 21a is formed at one end portion of the storage bag 21 and a bottom surface 21b (refer to FIG. 1) having a substantially oval shape is formed at the other end portion which is opposite to the opening 21a.

A bending portion 21c is provided with the bottom surface 21b. The bending portion 21c is formed along the width direction of the storage bag 21 approximately on the center of the bottom surface 21b. When the liquid M1 is discharged from the storage bag 21, the bending portion 21c is folded toward the inside of the storage bag 21 (refer to FIG. 7).

The material of the sheet member 24 which configures the storage bag 21 is preferably a material having flexibility and excellent in softness, and examples thereof include low density polyethylene, ethylene-vinyl acetate copolymer, a copolymer of polypropylene, a soft polyvinyl chloride, and the like. In addition, a blended material where at least two thermoplastic elastomers are blended to a polypropylene-based thermoplastic resin may be used.

As shown in FIG. 2 and FIG. 3, a connecting member of container side 23 is attached so as to clog the opening 21*a* of the storage bag 21. As in the same as of the bottom surface 21*b*, the connecting member of container side 23 is made in the shape of almost oval.

The connecting member of container side 23 has a cylindrical insert 26. The cylindrical insert 26 projects from one surface of the connecting member of container side 23 to the opposite side of the storage bag 21. As shown in FIG. 3, the cylinder hole 26*a* of the cylindrical insert 26 passes through from one surface to the other surface of the connecting member of container side 23. On the side surface of the cylindrical insert 26, a male screw part is formed. And the liquid suction tool 12 is connected to the connecting member of container side 23.

In the instant embodiment, one example where the connecting member of container side 23 is attached to the opening 21*a* of the storage bag 21 is explained, but the present invention is not limited thereto. For example, the cylindrical insert 26 may be directly attached to the storage bag 21.

[Liquid Suction Tool]

Figure 4:
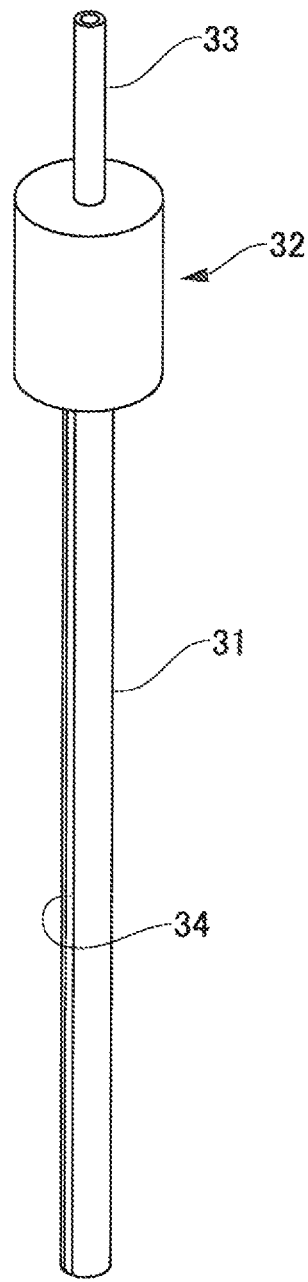
FIG. 4 is a perspective view of the liquid suction tool according to the first exemplary embodiment of the present invention.
Figure 5:
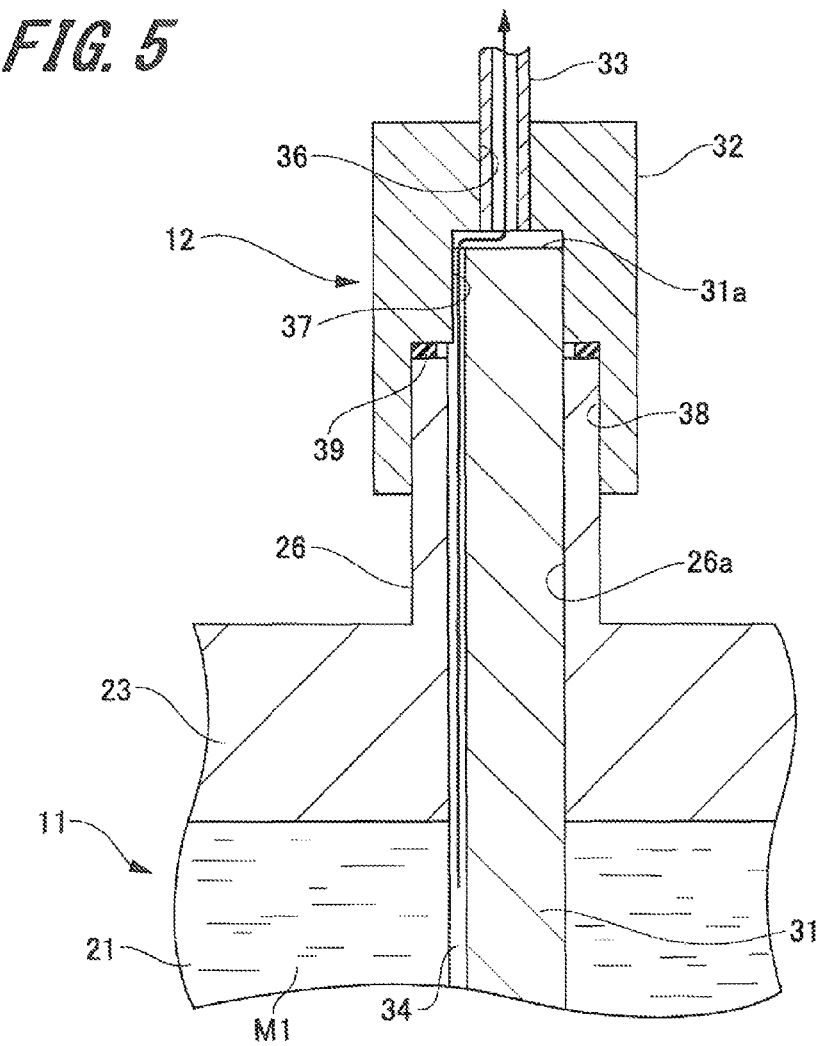
FIG. 5 is a cross-sectional view of the connection point of the liquid suction tool and the liquid storage container according to the first exemplary embodiment of the present invention.
Figure 6:
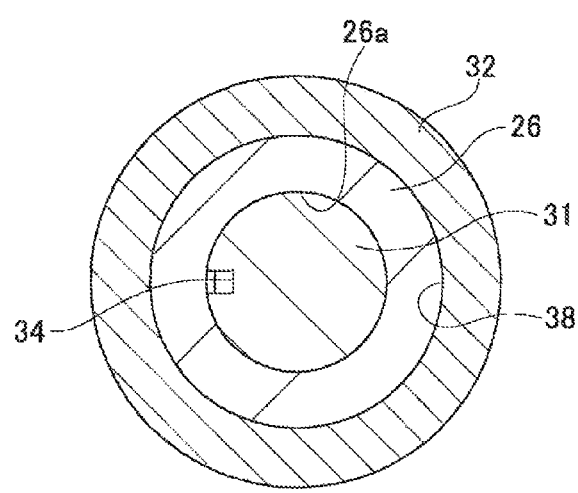
FIG. 6 is a T-T line cross-sectional view shown in FIG. 2.

FIG. 4 is a perspective view of the liquid suction tool 12, FIG. 5 is a cross-sectional view of the connection point of the liquid suction tool 12 and the liquid storage container 11, and FIG. 6 is a T-T line cross-sectional view shown in FIG. 2.

As shown in FIG. 4, the liquid suction tool 12 has the rod-like suction conduit 31, the connecting member 32 and a connecting piping 33. The connecting piping 33 is connected to the connecting tube 13 (refer to FIG. 1).

[Suction Conduit]

The suction conduit 31 is formed in a substantially columnar shape. The groove 34 where the liquid M1 passes is formed at the side surface of the suction conduit 31. As shown in FIG. 6, the groove 34 is a concave portion which is recessed from the side surface of the suction conduit 31 toward the axial center of the suction conduit 31. In addition, as shown in FIG. 3, the groove 34 is continuously formed from the one end portion 31*a* to the other end portion 31*b*, in the axial direction of the suction conduit 31.

In the exemplary embodiment, there has been explained the example of the groove 34 which is continuously formed from the one end portion 31*a* to the other end portion 31*b* of the suction conduit 31, but the present invention is not limited thereto. The length of the groove 34 to be formed may be, for example, a length from the one end portion 31*a* to the middle portion in the axial direction of the suction conduit 31. Additionally, a plurality of the grooves 34 may be formed on the side surface of the suction conduit 31.

In addition, as shown in FIG. 5, one end portion 31*a* of the suction conduit 31 is fixed to the connecting member 32. Furthermore, as shown in FIG. 3, the other end portion 31*b* of the suction conduit 31 is inserted from the cylindrical insert 26 of the connecting member 23 of the container side into the inside of the storage bag 21.

[Connecting Member]

As shown in FIG. 4, the connecting member 32 is formed in a substantially cylindrical shape. As shown in FIG. 5, the connecting member 32 has a first fitting surface 36, a second fitting surface 37, a screwing (threaded) section 38 and a sealing member 39.

The first fitting surface 36 is formed at one end portion in the axial direction of the connecting member 32. The connecting piping 33 is fitted into the first fitting surface 36. Note that the connecting tube 13 may be directly fitted into the first fitting surface 36 of the connecting member 32, without using the connecting piping 33.

The second fitting surface 37 which shows one example of a fixing portion is formed at the middle portion in the axial direction of the connecting member 32. One end portion 31*a* of the suction conduit 31 is fitted into the second fitting surface 37. Thereby, the one end portion 31*a* of the suction conduit 31 is fixed to the second fitting surface 37. Then, the suction conduit 31 and the connecting piping 33 are connected via the connecting member 32.

At this time, a gap is formed at the end portion on the connecting side between one end portion 31*a* of the suction conduit 31 and the first fitting surface 36 in the second fitting surface 37. Then, the liquid M1 passing through the groove 34 of the suction conduit 31 passes through the gap between one end portion 31*a* and the second fitting surface 37, and flows into the connecting piping 33 which is fitted into the first fitting surface 36.

Furthermore, the first fitting surface 36 may be provided at the position where the opening in the first fitting surface 36 at the second fitting surface 37 side faces the opening in the groove 34 of the suction conduit 31 which is fitted into the second fitting surface 37, on one end portion 31*a* side. Thereby, the liquid M1 passing through the groove 34 can flow to the connecting member 32 and the connecting tube 13, even without providing the gap between one end portion 31*a* of the suction conduit 31 and the second fitting surface 37. As a result, the amount of the liquid M1 remaining in the connecting member 32 can be reduced.

In the exemplary embodiment, there has been explained the example where the suction conduit 31 is fitted into the second fitting surface 37 as the fixing method of the connecting member 32 to the suction conduit 31, but the present invention is not limited thereto. Other various fixing methods such as adhesion and screwing can be used as the fixing method of the connecting member 32 to the suction conduit 31.

The screwing (threaded) section 38 which shows one example of the connecting member is formed at the other end portion in the axial direction of the connecting member 32. There is formed a screw groove which is screwed with the female screw of the cylindrical insert 26, on the inside wall of the screwing (threaded) section 38. Then, the connecting member 32 is attached to the cylindrical insert 26 by screwing the screwing (threaded) section 38 to the cylindrical insert 26. At this time, the suction conduit 31 is inserted into the inside of the storage bag 21 from the cylinder hole 26*a* of the cylindrical insert 26.

Additionally, an inner diameter of the screwing (threaded) section 38 is set larger than the inner diameter of the second fitting surface 37. In addition, a sealing member 39 is disposed at the end portion on the side of the second fitting surface 37 in the screwing (threaded) section 38. An O-ring, a packing, and the like are used as the sealing member 39.

Furthermore, in the exemplary embodiment, there has been explained the example in which the female screw is screwed with the screw groove as the connecting method of the connecting member 32 to the cylindrical insert 26, but is not limited thereto. Other various connecting methods such as fitting method and engaging method can be used as the connecting method of the connecting member 32 to the cylindrical insert 26.

1-3. Operation of Liquid Supply Unit

Next, the operation of the liquid supply unit 10 having the above configuration will be explained by referring to FIG. 1 to FIG. 8.

Figure 7:
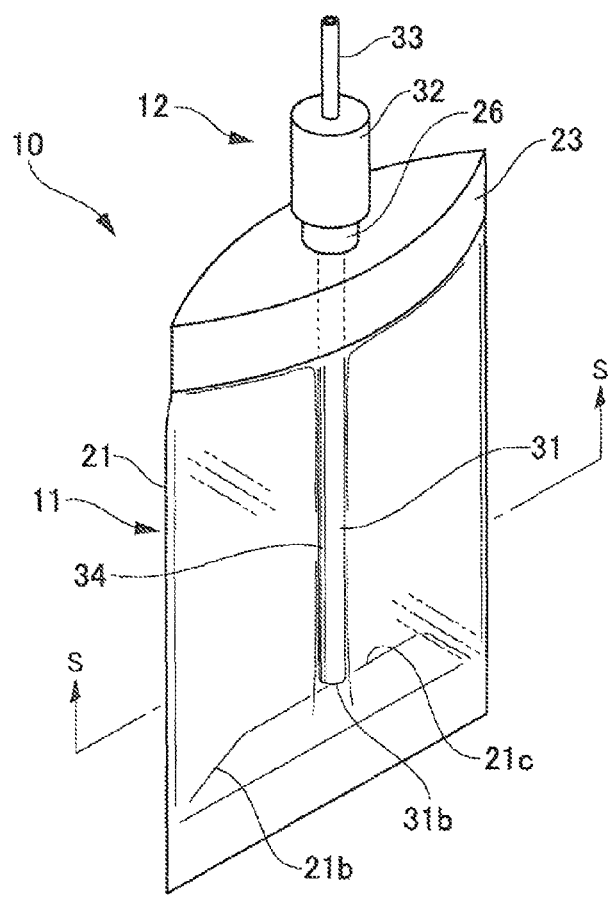
FIG. 7 shows the liquid supply unit according to the first exemplary embodiment of the present invention, and is a perspective view showing a state where the liquid is discharged from the liquid storage container.
Figure 8:
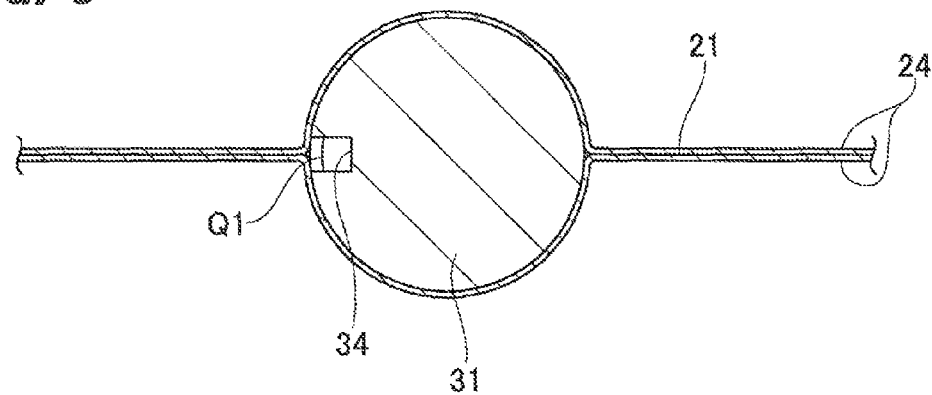
FIG. 8 is an S-S line cross-sectional view shown in FIG. 7.

FIG. 7 is a perspective view showing a state where the liquid is discharged from the liquid storage container 11, and FIG. 8 is an S-S line cross-sectional view shown in FIG. 7.

First, as shown in FIG. 2, a worker inserts the suction conduit 31 of the liquid suction tool 12 into the inside of the storage bag 21 from the cylindrical insert 26 of the liquid storage container 11. The storage bag 21 is previously filled with the liquid. Next, the worker attaches the connecting member 32 to the cylindrical insert 26 by screwing the screwing (threaded) section 38 of the connecting member 32 to the cylindrical insert 26. At this time, one end portion of the axial direction of the cylindrical insert 26 comes into contact with the sealing member 39 in the liquid-tight manner. Thereby it is possible to prevent the liquid M1 from leaking from the connected portion of the liquid suction tool 12 and the liquid storage container 11.

Next, as shown in FIG. 1, the worker drives the suction pump 14 (not shown) by control portion (not shown). By driving the suction pump 14, an air remaining in the storage bag 21 is discharged outward from the storage bag 21 via the suction conduit 31, the connecting piping 33 and the connecting tube 13.

When completing the discharging of the air remaining in the storage bag 21, as shown in FIG. 5, the liquid M1 stored in the storage bag 21 passes through the groove 34 formed in the suction conduit 31. The liquid M1 which passes through the groove 34 passes through the connecting member 32 and the connecting piping 33 to flow into the connecting tube 13 (refer to FIG. 1). Then, as shown in FIG. 1, the liquid M1 is supplied to each unit of the measuring device 1 from the connecting tube 13.

By forming the suction conduit 31 in the form of a solid rod, and forming the path of liquid M1 as the groove 34, the strength of the suction conduit 31 can be improved in comparison with the conventional suction conduit having the porous cylinder hole. As a result, it is possible to prevent the suction conduit 31 from bending and folding.

Further, by forming the suction conduit 31 in the form of a solid rod, it is possible to modify the shape of one end portion 31a and the other end portion 31b. For example, in order to insert the suction conduit 31 easily to the cylinder hole 26a of the cylindrical insert 26, the other end portion 31b can be modified to conical or hemispherical shape. In addition, it is possible to provide a notch with one end portion 31a of the suction conduit 31 to lock the connecting member 32.

Further, when the liquid M1 is sucked from the storage bag 21, as shown in FIG. 7, the storage bag 21 is deflated, and the bending portion 21c of the bottom surface 21b is folded toward the inside of the storage bag 21. Then, the bending portion 21c of the bottom surface 21b closes to the other end portion 31b of the suction conduit 31. Further, when the liquid M1 is sucked from the storage bag 21, as shown in FIG. 8, the inside wall of the storage bag 21 comes into tight contact with the side surface of the suction conduit 31, and then, the opening portion of the groove 34 in the suction conduit 31 is covered with the inside wall of the storage bag 21.

At this time, the sheet member 24 which forms the storage bag 21 and the groove 34 of the suction conduit 31 produce a space Q1 to form the path where the liquid M1 passes. As a result, even if the inside wall of the storage bag 21 comes into tight contact with the suction conduit 31, it is possible to draw the liquid M1 remaining in the storage bag 21.

As shown in FIG. 7, when the bottom surface 21b of the storage bag 21 is folded toward the inside of the storage bag 21, the other end portion 31b of the suction conduit 31 is disposed at the position where the portion would not close to the bending portion 21c or would not be contact with the bending portion 21c. Thereby, when the bottom surface 21b of the storage bag 21 is folded, it is possible to prevent the suction conduit 31 from interfering with the bottom surface 21b. As a result, it is possible to completely fold the bottom surface 21b of the storage bag 21, and thus, the amount of the liquid M1 remaining in the storage bag 21 can be reduced.

In order to reduce the amount of the liquid M1 remaining in the storage bag 21, it is preferable to reduce the distance between the other end portion 31b of the suction conduit 31 and the bending portion 21c at the folded manner.

The axial length of the suction conduit 31 is not limited to the above length. For example, when inserting to the storage bag 21, the other end portion 31b of the suction conduit 31 may contact with the bottom surface 21b.

Next, when completing the sucking of the liquid M1 stored in the storage bag 21, the pressure in the connecting tube 13 becomes lower than the atmospheric pressure, i.e. a negative pressure. Then, the pressure sensor 15 detects the negative pressure of the connecting tube 13. Next, the pressure sensor 15 performs notification to the worker, or sends the detected pressure information to the control portion (not shown). Then, the worker stops the drive of the suction pump 14 on the basis of the notification information. Alternatively, the control portion stops the drive of the suction pump 14 on the basis of the received information. Thereby, the operation in which the liquid supply unit supplies the liquid to the measuring device 1 is completed.

According to the exemplary embodiment, by setting the groove 34 as the liquid passage through which the liquid M1 passes, it is possible to downsize the depth or width of the groove 34 which forms the suction conduit 31, and to reduce the amount of the liquid M1 remaining in the suction conduit 31. In addition, since it is possible to downsize the depth or width of the groove 34 without reducing the diameter of the suction conduit 31, it is also possible to prevent decrease in the strength of the suction conduit 31. Furthermore, by only forming the groove 34 along the axial direction on the side surface of the rod-like member, it is possible to form the liquid passage through which the liquid M1 passes. Therefore, it becomes possible to easily produce the suction conduit 31.

2. Second Exemplary Embodiment

Next, the second exemplary embodiment of the liquid suction tool of the present invention will be explained by referring to FIG. 9 to FIG. 11.

Figure 9:
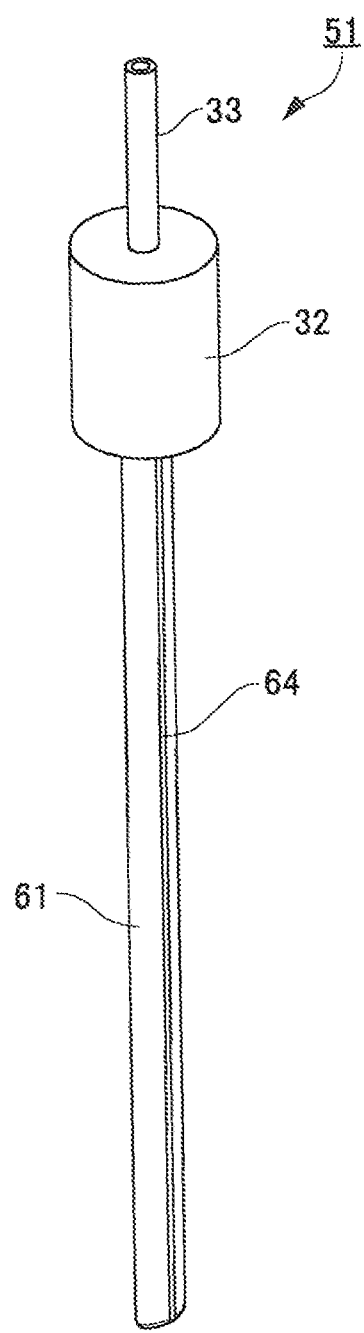
FIG. 9 is a perspective view of the liquid suction tool according to the second exemplary embodiment of the present invention.
Figure 10:
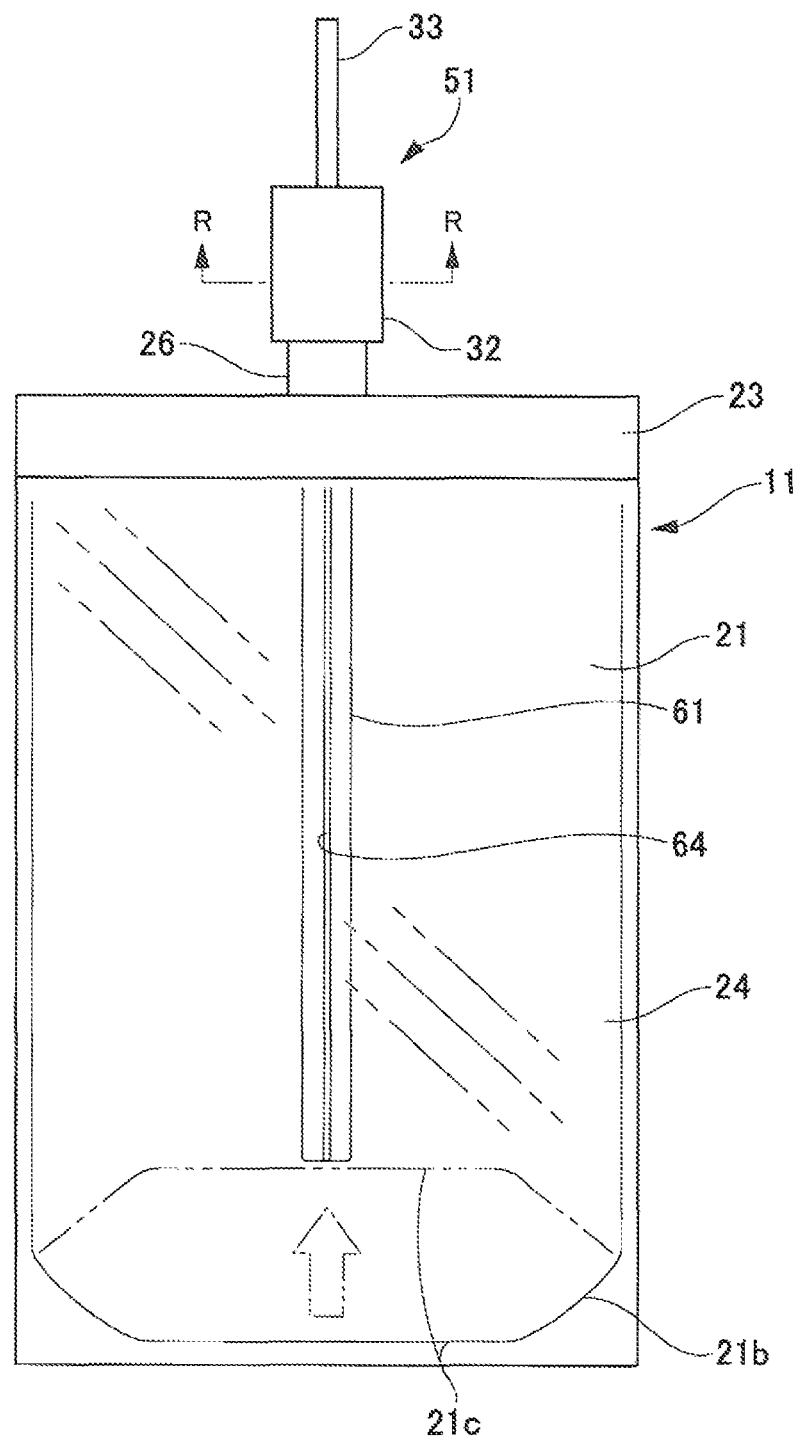
FIG. 10 is a front view of the liquid supply unit according to the second exemplary embodiment of the present invention.

FIG. 9 is a perspective view of the liquid suction tool according to the second exemplary embodiment, and FIG. 10 is a front view of the liquid supply unit having the liquid suction tool according to the second exemplary embodiment. FIG. 11 is an R-R line cross-sectional view shown in FIG. 10.

The different point of a liquid suction tool 51 according to the second exemplary embodiment from the liquid suction tool 12 according to the first exemplary embodiment is the shape of the suction conduit. Accordingly, here, explanation of the suction conduit is made, and the same symbols are attached to the parts common to the liquid suction tool 12 according to the first exemplary embodiment and the explanation thereof is omitted.

Figure 11:
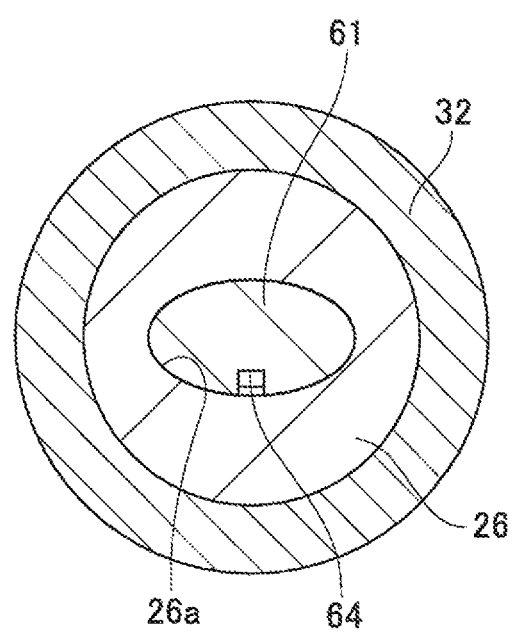
FIG. 11 is an R-R line cross-sectional view shown in FIG. 10.

As shown in FIG. 9 to FIG. 11, the liquid suction tool 51 has a rod-like suction conduit 61, the connecting member 32, and the connecting piping 33. The suction conduit 61 is formed in a substantially elliptic columnar shape. A groove 64 is formed along the axial direction, on the side surface of the suction conduit 61.

As shown in FIG. 10, the suction conduit 61 is inserted into the inside of the storage bag 21 so that the surface having a large curvature of radius on the side surface faces one surface of the sheet member 24 which forms the storage bag 21. Thereby, the storage bag 21 is deflated by discharging the liquid M1, and when the sheet members 24 facing each other are laminated, it is possible to enhance a degree of adhesion between the inside wall of the storage bag 21 and the side surface of the suction conduit 61. As a result, it is possible to reduce the gap formed between the storage bag 21 and the suction conduit 61 and to lower the amount of the liquid M1 remaining in the storage bag 21.

The other configuration is the same as in the liquid suction tool 12 according to the above first exemplary embodiment, and thus explanation thereof is omitted. The same actions and effects as those in the liquid suction tool 12 according to the above first exemplary embodiment can be obtained by using the liquid suction tool 51 having such a configuration.

Note that the present invention is not limited to the above embodiments which are explained above and shown in the drawings, and can be variously modified within the scope not departing from the gist of the inventions described in Claims. For example, in the above-described exemplary embodiment, there has been explained the example applied to a biochemical analyzer used for analysis of a living sample of blood or urea as the automated analyzer, but the embodiment is not limited to the example, and can be applied to a device that analyzes other various substances such as water quality and foods.

The shape of the suction conduit is not limited to a columnar shape and an elliptic columnar shape, and may be formed in other various shapes such as a square columnar shape, a shape obtained by flattening square, or the like.

EXPLANATION OF SYMBOLS 1 measuring device
10 liquid supply unit
11 liquid storage container
12, 51 liquid suction tool
13 connecting tube
14 suction pump
15 pressure sensor
21 storage bag
21a opening
21b bottom surface
21c bending portion
23 connecting member of container side
24 sheet member
26 cylindrical insert
26a cylinder hole
31, 61 suction conduit
31a one end portion
31b other end portion
32 connecting member
33 connecting piping
34, 64 groove
36 first fitting surface
37 second fitting surface (fixing portion)
38 screwing (threaded) section (connecting member)
39 sealing member
100 biochemical analyzer (automated analyzer)
M1 liquid
Q1 space

What is claimed is:

1. A liquid suction tool (12) attachable to a liquid storage container (11) that stores a liquid in a bag (21) positioned within the liquid storage container, said liquid to be supplied to a measuring device (1) of an automated analyzer (100) via piping (33) connected to a suction pump, the liquid suction tool comprising:
 a connecting member;
 a suction conduit (31, 61) being a solid rod having a solid cross section to be inserted into the bag positioned within the liquid storage container, said suction conduit having a concave groove recessed from a side surface of the rod and extending from one axial end of the rod along which liquid may pass to the connecting member (32);
 said connecting member (32) fixed to an end of the suction conduit; and
 a gap between the fixed end of the suction conduit and the connecting member; whereby the gap is configured to connect the concave groove of the suction conduit to the piping.

2. The liquid suction tool according to claim 1, wherein the concave groove is continuously formed from a first end to a second end of the suction conduit in an axial direction of the suction conduit.

3. A liquid supply unit comprising:
 a liquid suction tool (12);
 a liquid storage container (11); and
 a bag (21) that stores liquid positioned and supported within the container, said liquid to be supplied to a measuring device (1) of an automated analyzer (100) via piping (33);
 the liquid suction tool comprising:
 a connecting member;
 a suction conduit (31, 61) being a rod having a solid cross section to be inserted into the bag positioned within the liquid storage container, said suction conduit having a concave groove recessed from a side surface along which liquid may pass to the connecting member (32);
 said connecting member (32) being fixed to an end of the suction conduit; and
 a gap between the end of the suction conduit and the connecting member; whereby the gap is configured to connect the concave groove of the suction conduit to the piping;
 wherein a bottom surface of the bag being folded toward an inside of the bag and the suction conduit being disposed at a position of not being in contact with the bottom surface of the bag folded into the inside of the bag.

4. The liquid suction tool according to claim 1, wherein the connecting member (32) is formed in a cylindrical shape, and includes: a fixing surface (37) which is formed at one axial end and which is fixed to the suction conduit; and a internal screw surface (38) which is formed at the other axial end and which is connected with an externally threaded cylindrical insert (26) extending from the storage container,
 wherein the connecting member is provided with a sealing member (39) which contacts an end portion of the cylindrical insert and the connecting member in a liquid-tight manner.

5. An automated analyzer comprising:
 a measuring device that measures characteristics of a reaction solution obtained by causing a specimen to be measured to react with a reagent, and a liquid supply unit that supplies a liquid to the measuring device via piping connected to a suction pump, the liquid supply unit includes;

a liquid storage container that stores the liquid, and a liquid suction tool attached to the liquid storage container, the liquid storage container includes;

a storage bag which is formed of a sheet member having flexibility and which receives the liquid, and a cylindrical insert extending from the storage container, the liquid suction tool includes;

a suction rod having a solid cross section, said suction rod being inserted into the storage bag through the cylindrical insert, and a connecting member fixed at one axial end of the suction rod with a gap between the end of the suction rod and the connecting member and is attached to the cylindrical insert and which connects the suction portion and the storage bag, wherein a concave groove through which the liquid may pass is recessed from a side surface of the suction rod extending from one axial end of the rod to the connecting member.

\* \* \* \* \*